Oct. 3, 1961 P. DOT Plant Pat. 2,095
ROSE PLANT
Filed Nov. 22, 1960
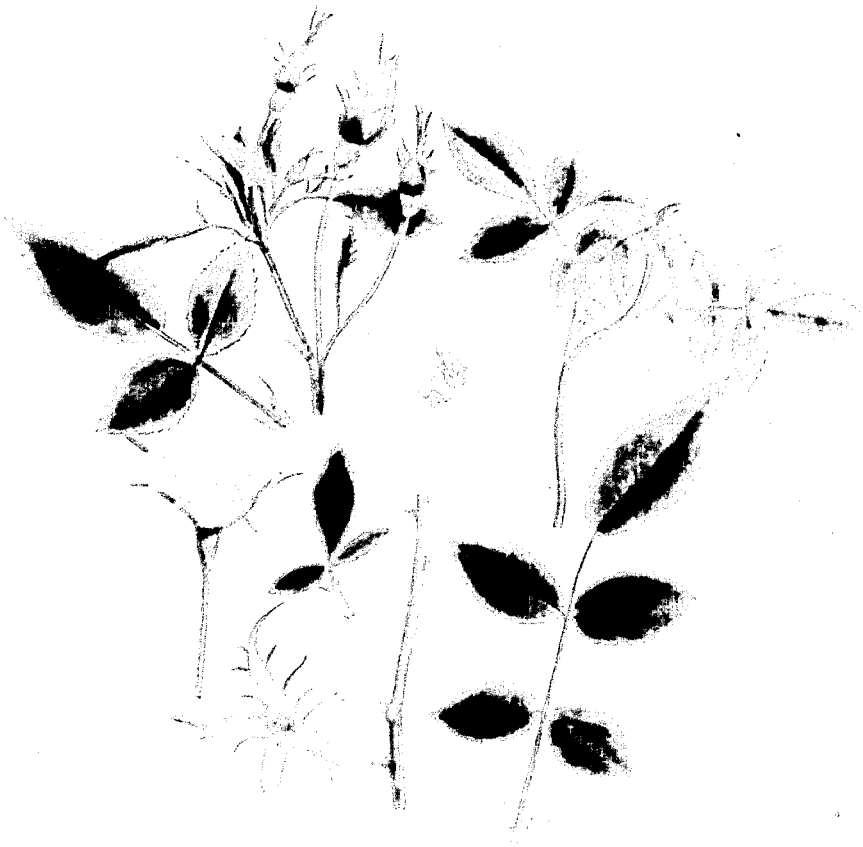
Inventor.
Pedro Dot
By: Robb & Robb
Attorneys.

United States Patent Office

Plant Pat. 2,095
Patented Oct. 3, 1961

2,095
ROSE PLANT

Pedro Dot, Barcelona, Spain, assignor to The Conard-Pyle Company, West Grove, Pa., a corporation of Pennsylvania Filed Nov. 22, 1960, Ser. No. 71,109
1 Claim. (Cl. 47—61)

The present invention relates to a new and distinct variety of rose plant of the miniature class, which was originated by me by crossing the variety "Perla de Montserrat" (unpatented) with the variety "Coralin" (unpatented).

The primary objective of this breeding was to produce a new variety of the miniature class, having both a low-growing plant habit and a novel flower color. This objective was fully achieved, along with other desirable improvements, as evidenced by the following unique combination of characteristics which are outstanding in the new variety and which distinguish it from its parents, as well as from all other varieties of which I am aware:

(1) A miniature plant habit, averaging from 8 inches to 12 inches in height;

(2) A miniature flower size, averaging from 1 inch to 1¼ inches in diameter;

(3) Perfectly formed blooms; and (4) A distinctive general color tonality of the blooms, ranging from Rhodomine Red to Spirea Red.

Asexual reproduction of the new variety by own-root cuttings, as performed at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; dwarf; outdoor; seedling; for garden decoration.

Class: Miniature.

Breeding: Seedling.

*Seed parent.*—"Perla de Montserrat."

*Pollen parent.*—"Coralin."

Propagation: Holds its distinguishing characteristics through succeeding propagations by cuttings.

*Flower*

Locality where grown and observed: West Grove, Pennsylvania, U.S.A.

Flowers borne: Usually several to stem; in irregular cluster; on short stems of normal strength.

Quantity of bloom: Abundant, both outdoors and in greenhouse.

Continuity: Continuous.

Fragrance: None.

Bud:

*Peduncle.*—Short; slender; erect; medium roughness; from few to medium number of green hairs. Color—Scheeles Green, Plate 860/3.

*Before calyx breaks.*—Size—small. Form—pointed; with a conspicuous neck; sometimes with foliaceous appendages on the surface of the bud; with slender, bristle-like foliaceous parts extending beyond the tip of the bud equal to ¼ or more of its length.

*As calyx breaks.*—Color—China Rose, Plate 024/1 on outer surface, with inner surface of petal Neyron Rose, Plate 623/1.

*As first petal opens.*—Size—very small. Form—short; ovoid. Color: outside—Magenta Rose, Plate 027/2, veined with near Rhodomine Pink, Plate 527/1; inside—Rhodomine Pink, Plate 527, grading to Rhodomine Pink, Plate 527/1 towards base of petal, with point of attachment Naples Yellow, Plate 403/3.

*Opening.*—Opens up well.

Bloom:

*Size (when fully open).*—Very small; from 1 inch to 1¼ inches.

*Petalage.*—Very double; from 40 to 45 petals; arranged regularly.

*Form.*—High-centered at first, but becoming cupped; petals being at first loosely rolled outward, and remaining loosely rolled outward at maturity.

Petals:

*Texture.*—Thin.

*Appearance.*—Inside—satiny. Outside—shiny.

*Shape.*—Outer petals—obovate. Intermediate petals—obovate. Inner petals—lanceolate.

This description of a newly opened flower was made from a rose grown in a greenhouse during the month of June at West Grove, Pennsylvania, U.S.A.:

*Color.*—Outer petal: outside surface—Rose Bengal, Plate 25/2, with point of attachment Pod Green, Plate 061/3; inside surface—Rhodomine Pink, Plate 527, often veined with Rose Bengal, Plate 25/1, with point of attachment Pod Green, Plate 061/3. Intermediate petal: outside surface—Rose Bengal, Plate 25/2, with point of attachment Pod Green, Plate 061/3; inside surface—Rhodomine Pink, Plate 527, often veined with near Rose Bengal, Plate 25/1, with point of attachment Pod Green, Plate 061/3. Inner petal: outside surface—Rose Bengal, Plate 25/2, with point of attachment Pod Green, Plate 061/3; inside surface—near Spirea Red, Plate 025/2, with point of attach-Pod Green, Plate 061/3.

This description was made from a rose that was open for three days in a greenhouse during the month of June at West Grove, Pennsylvania, U.S.A.:

*Color.*—Outer petal: outside surface—Spirea Red, Plate 025/2, usually veined with Spirea Red, Plate 025/3, and with point of attachment Pod Green, Plate 061/3; inside surface—Spirea Red, Plate 025/2, veined with Spirea Red, Plate 025/1, and with point of attachment Pod Green, Plate 061/3. Inner petal: outside surface—Spirea Red, Plate 025/1, grading to Spirea Red, Plate 025/3 over basal quarter of petal and extending in a narrow band along the center of the petal towards the apex, with point of attachment Pod Green, Plate 061/3; inside surface—Spirea Red, Plate 025/1, often streaked with Spirea Red, Plate 025/3, and with point of attachment Pod Green, Plate 061/3.

*General color effect.*—Newly opened flower—Rhodomine Pink, Plate 527. Three days open—Spirea Red, Plate 025/1.

*Behaviour.*—Drop off cleanly.

*Flower longevity.*—On bush in garden—long during June. Cut roses grown in greenhouse and kept at livingroom temperatures—long in June.

*Reproductive organs*

Stamens: Very few; arranged partly about pistils; mixed with petaloids.

Filaments: Very few; most with anthers; short. Color—Pod Green, Plate 061/3.
Anthers: All open at once; very small; occasionally an anther fused with a petaloid. Color—Lemon Yellow, Plate 4/1.
Pollen: Very sparse. Color—gold.
Pistils: Very few.
Styles: Uneven; very short; thin; separated.
Stigma: Color—white-yellow.
Ovaries: All enclosed in receptacle.
Hips: None observed.
Sepals: Permanent; spear-shaped.
Seeds: None observed.

*Plant*

Foliage:

*Leaves.*—Compound of 5–7 or occasionally 9 leaflets; normal abundance; very small; thin.

*Leaflets.*—Shape—oval. Apex—acute. Base—generally obtuse but sometimes acute. Margin—simply serrate.

*Color.*—Mature: upper surface—Spinach Green, Plate 0960/1; under surface—between Lavender Green, Plate 000761 and Lavender Green, Plate 000761/1. Young: upper surface—Spinach Green, Plate 0960/1, lightly overlaid and heavily margined with Oxblood Red, Plate 00823; under surface—near Sage Green, Plate 000861/1, veined and overlaid with Oxblood Red, Plate 00823/3.

*Rachis (the supporting stem of the compound leaf).*—Light. Upper side—grooved; hairy. Under side—smooth.

*Stipules.*—Short; very narrow; with very short points turning out at an angle of more than 45°.

*Disease resistance.*—Comparable to that of the average variety grown under the same cultural conditions at West Grove, Pennsylvania, U.S.A.

Growth:

*Habit.*—Dwarf; much-branched.

*Growth.*—Free.

*Canes.*—Very light.

*Main stems.*—Bright. Color—Lettuce Green, Plate 861. Prickles—few; color—near Pod Green, Plate 061, with base of prickle Lettuce Green, Plate 861. Hairs—none.

*Branches.*—Bright. Color—Lettuce Green, Plate 861. Prickles—few; color—near Pod Green, Plate 061. Hairs—none.

*New shoots.*—Dull. Color—Fern Green, Plate 0862/1, overlaid with Garnet Brown, Plate 00918/3. Prickles—few; color—Fern Green, Plate 0862/1, overlaid with Garnet Brown, Plate 00918/3 at base of prickle. Hairs—none.

I claim:

A new and distinct variety of rose plant of the miniature class, substantially as herein shown and described, characterized particularly as to novelty by the unique combination of a miniature plant habit, miniature flower size, perfectly formed blooms, and a distinctive general color tonality of the flowers ranging from Rhodomine Red to Spirea Red.

No references cited.